(12) United States Patent
Oncel et al.

(10) Patent No.: US 12,246,059 B2
(45) Date of Patent: *Mar. 11, 2025

(54) STABLE HYBRID FC FUSION G-CSF FORMULATION

(71) Applicant: ILKOGEN ILAÇ SANAYI VE TICARET A.S., Istanbul (TR)

(72) Inventors: Hatice Oncel, Istanbul (TR); Yilmaz Capan, Ankara (TR); Duygu Daglikoca, Ankara (TR); Huriye Erdogan Dagdas, Istanbul (TR); Adem Sahin, Ankara (TR); Meltem çorbacioglu, Istanbul (TR); Aylin Özkan, Istanbul (TR); Nagehan Sarraçoglu, Ankara (TR)

(73) Assignee: ILKOGEN ILAÇ SANAYI VE TICARET A.S., Istanbul (TR)

( * ) Notice: Subject to any disclaimer, the term of this patent is extended or adjusted under 35 U.S.C. 154(b) by 905 days.

This patent is subject to a terminal disclaimer.

(21) Appl. No.: 17/052,696

(22) PCT Filed: May 4, 2018

(86) PCT No.: PCT/TR2018/050208
§ 371 (c)(1),
(2) Date: Nov. 3, 2020

(87) PCT Pub. No.: WO2019/212429
PCT Pub. Date: Nov. 7, 2019

(65) Prior Publication Data
US 2021/0121529 A1    Apr. 29, 2021

(51) Int. Cl.
*A61K 39/395* (2006.01)
*A61K 9/00* (2006.01)
*A61K 9/08* (2006.01)
*A61K 38/19* (2006.01)
*A61K 47/02* (2006.01)

(52) U.S. Cl.
CPC .......... *A61K 38/193* (2013.01); *A61K 9/0019* (2013.01); *A61K 9/08* (2013.01); *A61K 47/02* (2013.01)

(58) Field of Classification Search
None
See application file for complete search history.

(56) References Cited

U.S. PATENT DOCUMENTS

| 8,586,048 B2 | 11/2013 | Yang et al. |
| 2003/0082679 A1 | 5/2003 | Sun et al. |
| 2016/0362473 A1 | 12/2016 | Wang et al. |

FOREIGN PATENT DOCUMENTS

| WO | WO-2009027437 A1 * | 3/2009 | ....... A61K 47/48215 |
| WO | 2012/165917 A1 | 12/2012 | |

OTHER PUBLICATIONS

International Search Report for PCT/TR2018/050208, dated Feb. 13, 2020.
Written Opinion for PCT/TR2018/050208, dated Feb. 13, 2020.

* cited by examiner

*Primary Examiner* — Yunsoo Kim
(74) *Attorney, Agent, or Firm* — Sughrue Mion, PLLC (57) ABSTRACT

A stable form of hybrid Fc fused Granulocyte Colony Stimulating Factor (G-CSF) formulation is disclosed. The formulation includes (i) a therapeutically effective amount of hybrid Fc fusion G-CSF, (ii) a buffer system, (iii) at least one stabilizer and (iv) at least one surfactant, and (v) optionally propylene glycol as organic solvent, suitable for administration via a subcutaneous (SC) route.

10 Claims, 2 Drawing Sheets
Specification includes a Sequence Listing.

SEQUENCE LISTING

```
<160> NUMBER OF SEQ ID NOS: 3

<210> SEQ ID NO 1
<211> LENGTH: 449
<212> TYPE: PRT
<213> ORGANISM: Artificial Sequence
<220> FEATURE:
<223> OTHER INFORMATION: Synthetic Construct (hy-Fc fused G-CSF monomer)

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30
```

```
Leu Gly Pro Ala Ser Ser Leu Pro Gln Ser Phe Leu Leu Lys Cys Leu
        35                  40                  45
Glu Gln Val Arg Lys Ile Gln Gly Asp Gly Ala Ala Leu Gln Glu Lys
 50                  55                  60
Leu Cys Ala Thr Tyr Lys Leu Cys His Pro Glu Glu Leu Val Leu Leu
 65                  70                  75                  80
Gly His Ser Leu Gly Ile Pro Trp Ala Pro Leu Ser Ser Cys Pro Ser
                 85                  90                  95
Gln Ala Leu Gln Leu Ala Gly Cys Leu Ser Gln Leu His Ser Gly Leu
                100                 105                 110
Phe Leu Tyr Gln Gly Leu Leu Gln Ala Leu Glu Gly Ile Ser Pro Glu
            115                 120                 125
Leu Gly Pro Thr Leu Asp Thr Leu Gln Leu Asp Val Ala Asp Phe Ala
        130                 135                 140
Thr Thr Ile Trp Gln Gln Met Glu Glu Leu Gly Met Ala Pro Ala Leu
145                 150                 155                 160
Gln Pro Thr Gln Gly Ala Met Pro Ala Phe Ala Ser Ala Phe Gln Arg
                165                 170                 175
Arg Ala Gly Gly Val Leu Val Ala Ser His Leu Gln Ser Phe Leu Glu
            180                 185                 190
Val Ser Tyr Arg Val Leu Arg His Leu Ala Gln Pro Arg Asn Thr Gly
        195                 200                 205
Arg Gly Gly Glu Glu Lys Lys Lys Glu Lys Glu Lys Glu Glu Gln Glu
210                 215                 220
Glu Arg Glu Thr Lys Thr Pro Glu Cys Pro Ser His Thr Gln Pro Leu
225                 230                 235                 240
Gly Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
```

Lys

<210> SEQ ID NO 2
<211> LENGTH: 384
<212> TYPE: PRT
<213> ORGANISM: Homo sapiens
<220> FEATURE:
<223> OTHER INFORMATION: amino acid sequence of human IgD constant
      region (Genbank accession No. P01880)

<400> SEQUENCE: 2

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
            20                  25                  30

Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys
    130                 135                 140

Glu Lys Glu Lys Glu Glu Gln Glu Glu Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
        195                 200                 205

Lys Val Pro Thr Gly Gly Val Glu Glu Gly Leu Leu Glu Arg His Ser
    210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
            260                 265                 270

Val Lys Leu Ser Leu Asn Leu Leu Ala Ser Ser Asp Pro Pro Glu Ala
        275                 280                 285

Ala Ser Trp Leu Leu Cys Glu Val Ser Gly Phe Ser Pro Pro Asn Ile
    290                 295                 300

Leu Leu Met Trp Leu Glu Asp Gln Arg Glu Val Asn Thr Ser Gly Phe
305                 310                 315                 320

Ala Pro Ala Arg Pro Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
            340                 345                 350

```
Tyr Thr Cys Val Val Ser His Glu Asp Ser Arg Thr Leu Leu Asn Ala
            355                 360                 365

Ser Arg Ser Leu Glu Val Ser Tyr Val Thr Asp His Gly Pro Met Lys
370                 375                 380
```

<210> SEQ ID NO 3
<211> LENGTH: 327
<212> TYPE: PRT
<213> ORGANISM: Homo sapiens
<220> FEATURE:
<223> OTHER INFORMATION: amino acid sequence of Partial human IgG4
      constant region (Genbank accession No. AAH25985)

<400> SEQUENCE: 3

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300
```

```
Cys Ser Val Met His Glu Ala Leu His Asn His Tyr Thr Gln Lys Ser
305                 310                 315                 320

Leu Ser Leu Ser Leu Gly Lys
                325
```

STABLE HYBRID FC FUSION G-CSF FORMULATION

CROSS REFERENCE TO RELATED APPLICATIONS

This application is a National Stage of International Application No. PCT/TR2018/050208 filed May 4, 2018.

INCORPORATION BY REFERENCE OF SEQUENCE LISTING

The content of the electronically submitted sequence listing, file name: Q258726_SubstituteSequence_Listing_ST25.txt; size: 9.5 KB; and date of creation: May 28, 2024, filed herewith, is incorporated herein by reference in its entirety.

DESCRIPTION

Technical Field

The present formulation is related to the stable liquid formulation compositions comprising hybrid Fc fused to Granulocyte Colony Stimulating Factor (G-CSF) molecules via peptide bond, suitable for administration via a subcutaneous (SC) route.

Prior Art

Granulocyte colony stimulating factor (G-CSF) is a protein that is essential for the proliferation and differentiation of granulocytes, particularly neutrophils. Granulocytes engulf and devour microbial invaders and cell debris and thus are crucial to infection response. However, they have only a 6-12 hour life span in the bloodstream and are destroyed as they function. As a result of their fast turnover, the granulocyte count falls rapidly and markedly upon bone marrow damage, for example from treatment with traditional cancer treatments, including chemotherapeutic agents and radiation, or immunologic disorders including AIDS (U.S. Pat. No. 7,208,473 B2).

Over the past years, it has been a great interest of many scientists to increase the effectiveness of naturally existing molecules or drugs by increasing in-vivo activity and/or reducing side-effects. Granulocyte colony-stimulating factor (G-CSF) is an example of which, drug-properties have been altered with time (N. Nicola, *Colony Stimulating Factors*, vol. 49, Marcel Dekker, Inc., New York, 1990).

A recombinant, methionyl human G-CSF (r-metHuG-CSF), a 175-residue protein, was produced first in *E. coli* (C. P. Hill, T. D. Osslund, D. Eisenberg, *The structure of granulocytecolony-stimulating factor and its relationship to other growth factors*, Proc. Natl. Acad. Sci. U.S.A. 90, 1993, 5167-5171). In the protein structure, there are two disulfide bonds, and one free cysteine residue, Cys17. Cys17 is known to be protonated at low pH and the protonated form is important for the stability of G-CSF (T. Arakawa, S. J. Prestrelski, L. O. Narhi, T. C. Boone, W. C. Kenney, *Cysteine 17 of recombinant human granulocyte-colony stimulating factor is partially solvent-exposed* (J. Protein Chem. 12, 1993, 525-531). The market name for r-metHuG-CSF is NEUPOGEN® (Filgrastim) and is used in the treatment of cancer therapy-induced neutropenia, bone marrow transplantation procedures, severe congenital neutropenia, aplastic anemia, myelodysplastic syndromes, and AIDS (Product Monograph: Neupogen® (filgrastim)—Amgen Canada).

Relatively short half-life (3.5-3.8 hrs) of filgrastim was positioned with NEULASTA® (PEG-Filgrastim) in which G-CSF is covalently linked to a polyethylene glycol chain that can increase circulation of G-CSF in the body with a half-life of 18-80 hrs (Product Monograph: Neulasta® (PEGFilgrastim)). PEGylation of G-CSF has no effect on the stability conditions, where the protein still needs a pH of 4.0 for long term storage at 2-8° C.

Another method to increase effectiveness is to use an immunoglobulin as a fusion platform. As described in U.S. Pat. No. 5,045,312, human growth hormone is conjugated to bovine serum albumin or mouse immunoglobulin by the use of a carbodiimide or glutaraldehyde as cross-linking agent. The conjugates have enhanced activity, when compared with unmodified growth hormone.

Modifications on Fc-domain such as altering glycosylation sites has known to improve therapeutic effect (R. J. Sola and K. Griebenow, *Effects of Glycosylation on the Stability of Protein Pharmaceuticals might improve therapeutic role*, J Pharm Sci. 2009 April; 98(4): 1223-1245). Additionally, when an active substance is fused to the Fragment crystallizable (Fc) region of an antibody, an extended circulation or clinical activity is also achieved. The addition of the Fc domain augments the hydrodynamic radius of the fused partner and provides an increased circulation, by interaction with Fc receptors, which in total hardens its clearance by the kidneys and increases its circulation duration (D. M. Czajkowsky, J. Hu, Z. Shao, and R. J. Pleass. *Fc-fusion proteins: new developments and future perspectives*, EMBO Mol Med. 2012 October; 4(10): 1015-1028).

Fusion proteins, as mentioned, are widely researched with an immunoglobulin (Ig) as a fusing-platform. Human Ig (hIg) widens into IgG, IgM, IgA, IgD, and IgE which then can be further classified into subtypes as human IgG1 (hIgG1), human IgG2 (hIgG2), human IgG3 (hIgG3), and human IgG4 (hIgG4) (Roitt et al., *Immunology* 1989, Gower Medical Publishing, London, U. K.; New York, N.Y). Igs are heterodimeric proteins that are comprised of four polypeptide chains, heavy chain (HC) and light chain (LC), connected thru disulfide bonds. Both HC and LC are comprised of a variable and a constant region. The constant region of the heavy chain may further sub-divided into three or four regions (CH1, CH2, CH3, and CH4). Contingent on the isotype, the Fc portion of the heavy chain constant region may comprise of hinge, CH2, CH3, and/or CH4 regions. IgG1, IgG2, and IgG4 have long serum half-lives of 21 days, while other IgGs have about a week. When fusion proteins formed through Fc portion of IgG of N-terminus of the CH1 region, the N-terminus of Fc region, or at the C-terminus of CH3 region of IgGs, enhanced stability and serum half-life could be achieved (H. W Schroeder, L. Cavacini, *Structure and Function of Immunoglobulins*, J Allergy Clin. Immunol. February 2010; 125 (202):41-52; Capon et al., *Designing CD4 immunoadhesins for AIDS therapy*, Nature 1989; 337: 525-531).

IgG fusion proteins could be formed via being fused to the extracellular domains of cell surface receptors or to cytokines and growth hormones (Capon et al., *Designing CD4 immunoadhesins for AIDS therapy*, Nature 1989. 337: 525-531; Mohler et al., *Soluble tumor necrosis factor (TNF) receptors are effective therapeutic agents in lethal endotoxemia and function simultaneously as both TNF carriers and TNF antagonists*, J. Immunology 1993. 151: 1548-1561).

However, unlike the fusion with the extracellular domains of cell surface receptors, the fusion of soluble proteins to IgGs leads to reduced biological activities, compared to non-fused cytokine or growth factors. The reason is that the chimeric proteins exist as dimers where two active proteins are in close proximity; this leads to a steric hindrance of fused-IgGs towards their target molecules. Therefore, this problem should be overcome to make an efficient fusion protein (Immunoglobulin fusion proteins, US 20120276097 A1).

The other limitation of the Fc fusion technology is the occurrence of undesired-immune responses. The Fc domain of the immunoglobulin has also effector functions such as antibody dependent cell-mediated cytotoxicity (ADCC) or complement-dependent cytotoxicity (CDC). This effector functions are generally achieved via interaction between the Fc region of the Ig and Fc receptors (FcR) on effector cells or via complement binding. Therefore, the blocking of effector functions of Fc should be performed to reduce the undesired responses such as cell death, cytokine release, or inflammation (Immunoglobulin fusion proteins, US 20120276097 A1).

Overall, it is known that usage of G-CSF based product such as filgrastim (Neupogen®) without any modification is limited due to its short half-life. Pegfilgrastim (NEULASTA®) has comparably an increased half-life, but it is know that PEG could have some adverse effects and Pegylation brings an additional production step. Fc fusion strategies provide opportunity to increase short half-life of proteins but one of the major limitations of the Fc fusion technology is the presence of undesired immune responses, as explained. The Hybrid Fc (hyFc) platform, which is the molecule of interest tested to be formulated and stabilized in this present invention, has been invented both to further improve plasma half-life of the conjugated drugs and to reduce cytotoxicity and immunogenicity (EP20080766022, U.S. Pat. No. 8,586,038B2). For this purpose, two different immunoglobulins having no ADCC and CDC response were combined genetically. Hybrid Fc is derived from combinations of human IgG subclasses or combinations of human IgD and IgG. The hybrid Fc is effective, when joined to a biologically active molecule, to increase serum half-life of the biologically active molecule as well as increase expression level of the polypeptide when a nucleotide coding for the Fc-polypeptide fusion protein is expressed. Thus, Hybrid Fc (hyFc)-Fused G-CSF also has a longer plasma half-life, efficient expression level, eliminated cytotoxicity and reduced immunogenicity (U.S. Pat. No. 8,586,048 B2). In this respect, hy-Fc fused G-CSF is a unique and originator molecule, where the Fc part itself is a fusion of two immunoglobulin molecules and this first fusion is further fused to the active molecule. As this structure requires attention to the stability of both the Fc fusion part and the G-CSF part, it is different than other regular Fc fusion drugs and requires additional different and unique solutions for constituting its stability. In this regard, for the present invention, literature studies about the stability of regular Fc fusion proteins were done but the invention itself was done as per the specific needs of this unique hy-Fc fused G-CSF.

When literature review is done, there are different formulation solutions for regular Fc fused drugs. The diverse biophysical and chemical properties of recombinant antibody and Fc-conjugate proteins require formulations in liquid and lyophilized forms of pH (4.0-8.5), buffers (acetate, citrate, phosphate), stabilizers (salts, sugars, amino acids), and/or surfactants (polysorbate 20 and polysorbate 80) to protect their integrity and efficacy during storage (S. M. Chamow, T. Ryll, B. H Lowman, and D. Farson, Eds., *Therapeutic Fc-Fusion Proteins*, Wiley-Blackwell: Hoboken, NJ, 2014).

Unlike intact monoclonal antibodies (mAbs) that are stabilized by inter- and intradomain interactions of Fc and Fab domains; Fc-conjugates are relatively unstable due to missing inter-domain stability (A. L Nelson., *Antibody fragments, MAbs.* 2010 January-February; 2(1): 77-83). Moreover, it is mostly the case that there exists more than one degradation pathway for an Fc-fusion protein. Often, while one formulation condition that stabilizes a molecule against one route of degradation, might stimulate another route of degradation. Therefore, it possesses both quite an importance and a challenge to establish an ideal formulation composition to an Fc fusion protein drug.

Formulation development requires identifying physical and chemical degradation pathways of the molecule. Once critical degradation pathways have been identified, it is an aim of a formulation scientist to develop an ideal composition of a formulation buffer comprising a buffering agent, stabilizer, and/or surfactant.

The stability of an Fc-fusion protein against chemical and physical degradation is often maximized in a narrow pH range (S. M. Chamow, T. Ryll, B. H Lowman, and D. Farson, Eds., *Therapeutic Fc-Fusion Proteins*, Wiley-Blackwell: Hoboken, NJ, 2014), hence, it is very important to screen the optimal pH. Besides pH, stabilizing agents such as sugars (sucrose, trehalose, and/or polyols) are also important components of Fc-conjugate formulations (Gokarn et al. *Excipients for Protein Dugs, Excipient Development for Pharmaceutical, Biotechnology, and Drug Delivery,* 2006). In addition, surfactants, such as polysorbates, also play important role in protein formulations. They are surface-active agents that compete with protein binding for the interface, therefore reducing interfacial tension and its harm to protein structures (T. A. Khan, H-C. Mahler, R. S. K. Kishore, *Eur. J. Pharm. Biopharm;* 2015 November 97: 60-67).

Aggregation in protein-based therapeutics is known to occur at every stage: in production, formulation, storage, shipping and even during administration. As such protein aggregation is a problem of significant magnitude for the biopharmaceutical industry, and despite enormous technical advances in recent years; it still continues to be a major obstacle in development. Therefore, the ability to predict, minimize, restrict and/or reverse protein aggregation is crucial to the viable manufacture and formulation of biotherapeutics. Unfortunately, the control of aggregation is a considerable challenge because the mechanisms of aggregation follow numerous pathways. Although much knowledge of aggregation mechanisms has been accumulated, currently it is still not possible to robustly predict a protein's propensity to aggregate. However, the current models of aggregation have identified two factors that govern stability; one is colloidal and the other is conformational stability.

Colloidal stability is determined by the balance of repulsive and attractive intermolecular interactions between protein molecules in solution. Conformational stability is defined as the difference in free energy between the folded and unfolded states of a protein molecule. Current techniques for predicting protein aggregation propensity are therefore based on the assessment of conformational and colloidal stabilities. These include in silico sequence/structure based predictions and determination of aggregation onset ($T_m$) as indicators of conformational stability and the determination of the osmotic second virial coefficient ($A_2$) as a measure of colloidal stability.

Leading to the present invention, a systematic research was performed for the specific needs of the unique and originator drug molecule hy-Fc-fused G-CSF. In order to provide empowerment of the long-acting G-CSF conjugate with stable liquid formulations, capable of retaining chemical and biophysical integrity of the active substance, formulation comprising a buffer in a certain pH range, stabilizer, surfactant and/or an organic moiety was invented.

In this present invention, stable formulations of HYBRID Fc FUSED G-CSF were evaluated and these stable formulations were selected based on chromatographic and electrophoretic purity, $A_2$, and $T_{onset}$ values. Long term stability of selected formulations is demonstrated with examples.

Description of the Problem

It is a particular challenge to develop the type of formulation as described herein to a fused drug, where the platform requires different chemical or biophysical stability rations than the one of the active substance that is fused to. In this present invention, it should also be noted that hy-Fc fusion platform (EP20080766022, U.S. Pat. No. 8,586, 038B2) is a unique and originator molecule and is different than other regular Fc platforms, thus requires different solutions for constituting its stability. In particular, other regular Fc platforms often include IgG2 or similar immunoglubulins' Fc region and the drug is directly fused to this single immunoglobulin's Fc region. However, hy-Fc platform is a combination of IgD and IgG subclasses, where the immunoglobulin Fc part itself forms a fusion and the fusion of the drug to this immunoglobulin part makes up the second fusion. Within this respect, all inventions explained herein, are completely specific to the described hy-Fc-G-CSF drug and have been developed per the specific needs for the stability of this unique molecule (U.S. Pat. No. 8,586,048 B2).

The hybrid Fc fusion G-CSF (hy-Fc-G-CSF) is represented by the following formula (I):

N'-G-Y-Z2-Z3-Z4-C'     Formula (I)

wherein
G is a G-CSF;
N' is the N-terminal of a polypeptide and C' is the C-terminal of a polypeptide;
Y is an amino acid sequence having 5 to 64 consecutive amino acid residues from the amino acid residue at position 162 toward the N-terminal, among the amino acid residues at positions from 99 to 162 of SEQ ID NO: 2;
Z2 is an amino acid sequence having 4 to 37 consecutive amino acid residues from the amino acid residue at position 163 toward the C-terminal, among the amino acid residues at positions from 163 to 199 of SEQ ID NO: 2;
Z3 is an amino acid sequence having 71 to 106 consecutive amino acid residues from the amino acid residue at position 220 toward the N-terminal, among the amino acid residues at positions from 115 to 220 of SEQ ID NO: 3; and
Z4 is an amino acid sequence having 80 to 107 consecutive amino acid residues from the amino acid residue at position 221 toward the C-terminal, among the amino acid residues at positions from 221 to 327 of SEQ ID NO: 3.

In this respect, hyFc fused G-CSF is a unique and originator molecule, where the Fc part itself is a fusion of two immunoglobulin molecules and this first fusion is further fused to the active molecule.

Figure 1:
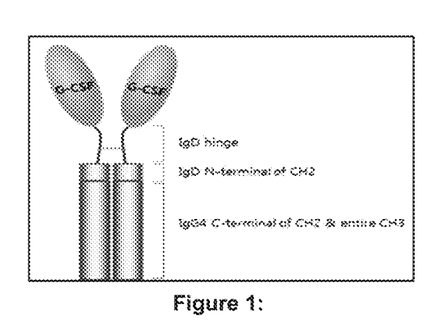
FIG. 1. Schematic protein structure of hy-Fc fused G-CSF

For use in the present invention, the hy-Fc platform and G-CSF have amino acid sequence of humanized organisms. No additional fusion reaction is used, as the fusions both between the IgD and IgG and between G-CSF and the immunoglobulin part are provided through single genetic code and single transcription-translation reaction. The peptide bond between G-CSF and hy-Fc platform is through Proline-Arginine. Amino acid sequence of hy-Fc fused G-CSF monomer is below. Signal, G-CSF, N-terminal and hy-Fc sequences are denoted in the corresponding format. Schematic protein structure of hy-Fc fused G-CSF is shown in FIG. 1.

MAGPATQSPMKLMALQLLLWHSALWTVQEATPL GPASSLPQSFLLKCLEQVRKIQG DGAALQEKLCAT YKLCHPEELVLLGHSLGIPWAPLSSCPSQALQLA GCLSQLHSGL FLYQGLLQALEGISPELGPTLDTLQLD-VADFATTIWQQMEELGMAPALQPTQGAMP AFASA-FORRAGGVLVASHLQSFLEVSYRVLRHLAQPRNT-GRGGEEKKKEKEKEEQVDGVEVHNAKTKPREEQFN-STYRVVSLTVLHQDVLNGKEYKCKVSNKGLPSSIEK TISKAKGCPREPOVYTLPPSQEEMXOVSLTCLVKG FYPSDIAVEWESNGQPENN YKTTPPVLDSDGSFFLY-SRLTVDKSRWOQEGNVFSCSVMNHEALHNHYTCK-SLSLSLG K (SEQ ID NO: 1)
MAGPATQSPMKLMALQLLLWHSALWTVQEA*TPLGP*ASSLPQSFLLKCLE

QVRKIQGDGAALQEKLCATYKLCHPEELVLLGHSLGIPWAPLSSCPSQA

LQLAGCLSQLHSGLFLYQGLLQALEGISPELGPTLDTLQLDVADFATTI

WQQMEELGMAPALQPTQGAMPAFASAFQRRAGGVLVASHLQSFLEVSYR

VLRHLAQP<u>RNTGRGGEEKKKEKEKEEQEERETKTPECPSHTQPLGVFLF</u>

<u>PPKPKDILMISRIPEVTCVVVDVSQEDPEVQFNWYVDGVEVHNAKTKPR</u>

<u>EEQFNSTYRVVSVLTVHQDWLNGKEYKCKVSNKGLPSSIEKTISKAKGQ</u>

<u>PREPQVYTLPPSQEEMTKNQVSLTCLVKGFYPSDIAVEWESNGQPENNY</u>

<u>KITPPVLDSDGSFFLYSRLTVDKSRWQEGNVESCSVMHEALHNHYTQKS</u>

<u>LSLSLGK</u>

In this invention it is found that, the stability of the molecule is mostly affected by and prone to hydrolysis at lower pH values (pH<5.0) at the G-CSF junction site and di-sulfide shuffling at high pH values (pH>6.5). G-CSF has two disulphide bonds formed by homologous cysteine residues and an extra cysteine residue at position at 17, which cannot participate in intramolecular disulfide bonds. The disulphide bonds in these molecules stabilize the structures and make them resistant to relatively harsh treatment (some proteases, high temperatures, denaturing solvents, extreme pH), which do lead to denaturation after reduction of disulfide bonds (Nicos A. Nicola, *The waiter and Eliza Hall Institute of Medical Research, "Granulocyte Colony Stimulating Factor"*, p. 77-100).

Additionally, in-house studies demonstrated that hy-Fc fused G-CSF is no or hardly soluble between pH 5.3-6.0 and it is known that G-CSF itself is stable and active at around pH 4.0 (T. Arakawa, S. J. Prestrelski, L. O. Narhi, T. C. Boone, W. C. Kenney, *Cysteine 17 of recombinant human granulocyte-colony stimulating factor is partially solvent-exposed, J. Protein Chem.* 12 (1993) 525-531). Once the crucial route that leads to degradation has been specified, therefore, it is the aim is to ensure the long term stability of the active Fc-fusion molecule.

DESCRIPTION OF THE INVENTION

It is therefore the focus of present invention to provide liquid formulation compositions comprising long-acting G-CSF molecules fused via peptide link to a hybrid-Fc (hy-Fc), monoclonal antibody-like platform. The invented formulation for recombinant human G-CSF-hyFc should have especially a suitable pH, stabilizer, surfactant and/or an organic solvent that enables high stability both to the link between G-CSF and hy-Fc platform and between the hy-Fc platform itself, without disturbing G-CSF activity and the function of hy-Fc platform.

A "stable" formulation or drug product is one in which the G-CSF molecule therein essentially retains its biophysical and chemical stability and integrity upon storage. Stability of the G-CSF molecule formulations can be measured at selected temperatures after selected time periods.

One skilled in the art would be aware of that the stability of the hy-Fc fused G-CSF molecule highly depends on its formulation and hence it is essential for the stability of the drug product to protect its physical and chemical integrity upon storage. Change in purity, biophysical properties and efficacy of Fc-fused G-CSF molecule is the main indicator of stability, thus should be monitored at chosen temperatures in definite time intervals.

The term 'preparation' refers to prepared aqueous formulation. The preparation which comprises therapeutically effective amount of hybrid Fc fused G-CSF, at least one stabilizer, at least one surfactant and a buffer system used for adjusting the pH of the solution.

The present invention leads to invent a formulation for a hy-Fc fused G-CSF drug by an ideal combination of a buffering agent and/or surfactant and/or stabilizer and/or organic solvent.

The liquid formation according to the present invention comprises a stable form of hybrid Fc fused Granulocyte Colony Stimulating Factor (G-CSF) formulation comprising (i) a therapeutically effective amount of hybrid Fc fusion G-CSF, (ii) a buffer system, (iii) at least one stabilizer and (iv) at least one surfactant, and (v) optionally propylene glycol as organic solvent, wherein the pH value of the preparation is between 3.8 and 6.5, preferably between 4.0 and 4.6.

The term "therapeutically effective amount" refers to an amount which, when administered to a living subject, achieves a desired effect on the living subject. Typically, the therapeutically effective amount of G-CSF (Neulasta EMA document) is 6 mg per single-use. The therapeutically effective amount of hybrid Fc fused G-CSF is 50-400 mcg/kg, preferably 150-250 mcg/kg, whereas the therapeutically effective amount of G-CSF within hybrid Fc fused G-CSF is 20-160 mcg/kg, preferably 50-100 mcg/kg. To provide this therapeutic effect the concentration of the stable form of hybrid Fc fused G-CSF used in the present invention is on the order of 10 mg/mL to 80 mg/mL, and preferably on the order of 20 mg/mL to 40 mg/mL.

A "stabilizer" promotes stability of polypeptide components, thereby maintaining their therapeutic effectiveness. Sugars or sugar alcohols may also be included in the stabilized liquid polypeptide-containing pharmaceutical compositions of the present invention. Any sugar such as mono-, di-, or polysaccharides, or water-soluble glucans, including for example fructose, glucose, mannose, sorbose, xylose, maltose, lactose, sucrose, dextran, pullulan, dextrin, cyclodextrin, soluble starch, hydroxyethyl starch and carboxymethylcellulose-Na may be used. Sugar alcohol is defined as a C4-C8 hydrocarbon having a —OH group and includes, for example, mannitol, sorbitol, inositol, galacitiotol, dulcitol, xylitol, and arabitolm. The sugars or sugar alcohols mentioned above may be used individually or in combination. There is no fixed limit to the amount used, as long as the sugar or sugar alcohol is soluble in the liquid preparation and does not adversely affect the stabilizing effects achieved using the methods of the invention. Preferably, the sugar or sugar alcohol concentration is between about 1.0 w/v % and about 15.0 w/v %, preferably between about 2.0 w/v % and about 10.0 w/v %, more preferably between 3.0 w/v % and 7.0 w/v % based on the total volume of the liquid formulation. In this invention, the stabilizer is sorbitol wherein weight ratio of sorbitol to protein is between 3:2 to 7:2, preferably 5:2.

The term "buffer system" refers to one or more components that when added to an aqueous solution is able to protect the solution against variations in pH when adding acid or alkali, or upon dilution with a solvent. Thus, buffer solution plays an important role to stabilize hy-Fc-G-CSF in the liquid formulation. There can be used acetate, phosphate, glycinate, carbonate, citrate, histidine, tris-(hydroxymethyl)-aminomethane (Tris) buffers and the like, in which case, sodium, potassium or ammonium ions can serve as counterion. The buffers mentioned above may be used individually or in combination. An "acid" is a substance that yields hydrogen ions in aqueous solution. A "pharmaceutically acceptable acid" includes inorganic and organic acids which are non-toxic at the concentration and manner in which they are formulated. A "base" is a substance that yields hydroxyl ions in aqueous solution. "Pharmaceutically acceptable bases" include inorganic and organic bases which are non-toxic at the concentration and manner in which they are formulated. In this invention, the buffer system comprising sodium acetate trihydrate and acetic acid/sodium hydroxide is selected.

A "surfactant" is a surface active molecule containing both a hydrophobic portion (e.g., alkyl chain) and a hydrophilic portion (e.g., carboxyl and carboxylate groups). Surfactant may be added to the formulations of the invention. Surfactants suitable for use in the formulations of the present invention selected from the group consisting of a polysorbate-based non-ionic surfactant and a poloxamer-based non-ionic surfactant or a combination thereof. The liquid formulation of the present invention may comprise sorbitol as the non-ionic surfactant preferably at a concentration of from 0.08% (w/v) to 0.15% (w/v) based on the total volume of the liquid formulation.

An "organic solvent" is referred herein to Propylene Glycol (PG), a semi-polar component that aimed to reduce the acid mediated hydrolysis reaction taking place at low pH by reducing the aqueous content in/around protein. Propylene glycol or 1,2-dihydroxypropane or 1,2-propanediol, is a clear, colorless, viscous, practically odorless liquid with a density of 1.038 g/cm$^3$ at 20° C. and a molecular weight of 76.095. It is miscible with and in water, acetone and chloroform. PG monographs are included in the PhEur, the USP and the JP; and is commonly used as an excipient in a variety of drugs; and it is also authorized in food products and cosmetics (Background review for the excipient propylene glycol EMA/CHMP/334655/2013). The liquid formulation of the present invention may comprise Propylene Glycol as the organic solvent at a concentration of 20% (v/v) or less based on the total volume of the liquid formulation.

Methods for Selecting Ideal Fc Fused G-CSF Formulations of Invention:

The pH of the drug product may be determined by the potentiometric analysis described in the USP <791>.

Concentration of each sample may be determined via UV test from the absorbance measurement at 280, 320, 325, 330, 335, 340, 345, 350 nm each. From the total absorbance at 280 nm subtract the absorbance (at 320, 325, 330, 335, 340, 345, 350 nm) attributed to light scattering. The protein concentration in the test solution may be calculated by applying Lambert-Beer equation with a corrected absorbance and an extinction coefficient value of 1.03 ml/cm*g.

Differential scanning calorimetry may be a technique used to determine thermodynamic stability of proteins. It measures the amount of heat that is absorbed or released from biomolecules in solution during heating or cooling. Native proteins respond to heating by unfolding (thermal denaturation) at a characteristic temperature ($T_{onset}$). Nano DSC, TA instruments (New Castle, USA), may be the preferred method to determine the denaturation temperature and denaturation enthalpy of proteins and other macromolecules in solution with the versatility and precision to perform molecular stability screenings. To do that, samples are dialyzed against the corresponding formulation buffer and diluted to 1 mg/mL for further use in DSC instrument. The scan rate is 1° C./min heating and cooling with temperature range of 20-100° C.

Composition-Gradient-Multi-Angle Static Light Scattering, GC-MALS, may be used to determine interactions between protein molecules in solution by changes in their light scattering behavior at different concentrations. With series of light scattering measurements the second virial coefficient $A_2$, which is a characteristic parameter to evaluate molecule interactions, may be calculated. A Calypso II CG-MALS system, Wyatt Technology Europe (Dernbach, Germany), is used to supply the MALS detector with the concentration gradient of the analyte. The sample is loaded on one syringe pump of the system and the dialysis buffer on another syringe pump of the system. Ten equidistant concentration steps from 5 mg/mL to 0.5 mg/mL are applied in each measurement by diluting the sample with dialysis buffer. At each gradient step 1 mL of sample is injected into the MALS detector. The resulted light scattering signal is recorded over a time period of 180 sec. Zimm plot analysis may be performed with Calypso software version 2.1.3.

The turbidity of the samples may be determined using a 2100 AN turbidimeter (Hach Lange, Dusseldorf, Germany) according to the European Pharmacopeia. Calibration of the system is done by mixing Hydrazine sulfate and Hexamethylenetetramine to prepare primary opalescent suspension and then to further dilute standard of opalescence. The detector measures the light that is scattered at a 90° angle from the sample, together with the reflected light in front of the sample along with the transmitted light directly through the sample. The measuring results are given in NTU which is the ratio of the 90° angle scattered light measured to the sum of the components of reflected and transmitted values. Preparation of the Reference Solution for the Calibration of the Turbidimeter.

|  | I | II | II | IV |
|---|---|---|---|---|
| Standard of opalescence | 5.00 mL | 10.0 mL | 30.0 mL | 50.0 mL |
| Purified water | 95.0 mL | 90.0 mL | 70.0 mL | 50.0 mL |

To test the identity and purity of the molecule, electrophoretic properties of the hy-Fc fused G-CSF in terms of molecular weight and isoelectric point are monitored.

Sodium Dodecyl Sulfate Polyacrylamide Gel Electrophoresis (SDS-PAGE) analysis may be performed for hy-Fc fused G-CSF to compare the molecular weight with the one of in-house reference standard. The drug product and the in-house reference standard is diluted to 500 μg/mL using deionized water, and is made to 3 μg/20 μL using NuPAGE® LDS sample buffer (4×) and deionized water. It is loaded on the NuPAGE® Novex 4-12% Bis-tris gel (1.0 mm, 10 well) for electrophoresis. Isoelectric focusing gel electrophoresis may be used to identify hy-Fc fused G-CSF's isoelectric point range to the in-house reference standard. The drug product and the in-house reference standard are diluted to 1 mg/mL using deionized water, and made to 10 μg/20 uL using Novex® IEF sample buffer 2×). Isoelectric focusing is carried out using Novex® pH 3-10 IEF gel 1.0 mm, 10 well.

Purity of hy-Fc fused G-CSF in terms of monomeric and hydrophobic properties may be separated and monitored with liquid chromatographic techniques.

Size Exclusion Chromatography (SEC) may be the preferred method to separate molecules based on their size hence the high molecular weight species (HMW) and degraded species by using 2695 Alliance HPLC (Waters). Separation is achieved by the differential molecular exclusion or inclusion as the molecules migrate along the length of the column. The drug substance is diluted to 1 mg/mL and separated using the TSK-GEL G3000SWxL (7.8*300 mm) column and TSK-GEL G3000SWxL (6*40 mm) (TOSOH Bioscience) guard column. Mobile phase is composed of 50 mM phosphate buffer: sodium phosphate dibasic 5.34 g, sodium phosphate monobasic 3.12 g, sodium chloride 8.76 g in 1 L deionized water which are mixed with acetonitrile in 9:1 (v/v) ratio, where the final pH is 7.0. Flow rate 0.5 mL/min and detection wavelength of 214 nm are applied for 30 min. The % area of main peak to total area according to analysis result is calculated wherein the output indicates the monomeric purity.

Reverse Phase-High Performance Chromatography (RP-HPLC) may be another method to check purity via separating them by means of hydrophobicity. RP-HPLC is used to check impurities and retention time of Fc-fused G-CSF variants and truncated forms by using 2695 Alliance HPLC (Waters). A concentration of 1 mg/mL of drug in corresponding formulation buffer is separated by using the Vydac 214TP C4 column (4.6*250 mm) (Grace, Vydac) column and guard column 214MS C4, 5 μm, 7.5×4.6 mm (Grace, Vydac). Mobile phase is composed of 0.15% trifloroacetic acid (TFA) in deionized water and 0.15% TFA in Acetonitrile, at a flow rate of 0.5 mL/min. Detection wavelength of 220 nm is applied for 35 minutes and the % area of main peak to total area according to analysis result is monitored.

A better understanding of the present invention may be obtained through the following examples, which are set forth to illustrate but are not to be constructed as the limit of the present invention. These examples describe the development of liquid formulation comprising full length hyFc-Fused G-CSF described in U.S. Pat. No. 8,586,048 B2.

Example 1: Selection of Ideal pH and Buffer Component for HyFc-Fused G-CSF Formulation A buffering reagent is necessary to keep the targeted pH and stability of the protein, where it is known to be active. For the invention of a liquid formulation, buffers are initially screened by measuring the denaturation onset ($T_{onset}$) as indicators of conformational stability and the determination of the osmotic second virial coefficient ($A_2$) as a measure of colloidal stability.

In this invention, for compounding of the samples, formulations were prepared by dialysis. The drug substance was filled into preconditioned dialysis tubes and incubated for 2 hours in formulation buffer. After 2 hours, the formulation buffer was exchanged and the samples were incubated for 2 hours in fresh buffer. Dialysis was completed over night by incubation of the samples in fresh formulation buffer. After dialysis, the samples were removed from the dialysis tube and the pH as well as the concentration of the samples was checked. Where necessary, the pH was adjusted with pharmaceutical grade acid or base. Where necessary, the concentration was adjusted by dilution or concentration via ultra-filtration.

Preliminary lab scale measurements were done by means of formulation screening study to monitor colloidal stability, measured by Composition-Gradient Multi-Angle Static Light Scattering (CG-MALS) method, and thermodynamic properties, measured by Differential Scanning Calorimeter (DSC), of 20 mg/mL hy-Fc fused G-CSF in: 10 mM Sodium acetate at pH 3.8, 4.2, 4.6 and 5.2; 10 mM Histidine-hydrochloric acid at pH 5.2, 6.5 and 7.0; 10 mM Sodium-phosphate at pH 6.5 and 7.5; 10 mM Histidine-acetate at pH 6.5 and 7.0; 10 mM Tris-hydrochloric acid at pH 7.5 and 10 mM Tris-acetate at pH 7.5.

TABLE 1

Conformational and colloidal stability evaluation of 20 mg/mL hy-Fc fused G-CSF in different pH and buffer component

| pH | Buffer [10 mM] | $A_2$ [mol*mL*g$^{-2}$] | $T_{onset}$ {° C.} |
|---|---|---|---|
| 3.8 | Na/acetate | 63.7 | 45.6 |
| 4.2 | Na/acetate | 15.3 | 48.7 |
| 4.6 | Na/acetate | 5.87 | 52 |
| 5.2 | Na/acetate | −2.7 | 50.9 |
| 5.2 | His/HCl | −1.99 | 50.6 |
| 6.5 | His/HCl | 1.04 | 52.6 |
| 6.5 | His/acetate | 2.7 | 53.5 |
| 6.5 | NaPO$_4$ | −1.66 | 54.4 |
| 7 | His/HCl | 15 | 55 |
| 7 | His/acetate | 13.9 | 54.6 |
| 7.5 | Tris/HCl | 3.03 | 54.2 |
| 7.5 | NaPO$_4$ | 0.58 | 50.1 |
| 7.5 | Tris/acetate | 2.68 | 54.9 |

According to the results shown at Table 1, it was observed that increasing pH increased the $T_{onset}$ value and the $T_{onset}$ value is upper than 40° C. in all pH conditions. On the other hand, $A_2$ value found negative in pH 5.2 (using Na/acetate, His/HCl buffers), pH 6.5 (using NaPO$_4$ buffer). Negative $A_2$ value indicates colloidal instability. Near pI value of hy-Fc-fused G-CSF (pH 5.3-6.0), less repulsive and even attractive interactions between molecules were observed. At pH region from 6.5 to 7.0, higher colloidal stability in histidine-hydrochloric acid and histidine-acetate buffer systems than in sodium phosphate systems were revealed. Thus, in the current invention, based on A2 values and Tonset values, the pH conditions of 3.8 (Na/acetate), 4.2 (Na/acetate), 4.6 (Na/acetate), 6.5 (His/acetate) and 7.5 (His/acetate), were revealed to be favoring colloidal and thermodynamic stability of hy-Fc fused G-CSF.

Example 2: Evaluation of Sodium Chloride Addition on Stability of HyFc-Fused G-CSF Formulation Effects of other formulation excipient on $T_{onset}$ and $A_2$ values of the selected formulation were investigated in further studies, using pH 4.2 Na/acetate buffered and pH 6.5 His/acetate buffered formulations, based on the results provided in Example 1. For this study, siliconized container was chosen as packaging system. Pre-sterilized 1 mL oil siliconized glass syringe were filled with the samples under laminar flow. Stoppers were placed by a stoppering machine. Firstly, for evaluation of tonicity effect on stability a salt component of 150 mM sodium chloride was added to formulation. Then colloidal and conformational stability were evaluated described above.

TABLE 2

Conformational and colloidal stability evaluation of 20 mg/mL hyFc fused C-SF in 150 mM sodium chloride containing formulations

| pH | Buffer [10 mM] | Sodium chloride [mM] | $A_2$ [mol*mL*g$^{-2}$] | $T_{onset}$ {° C.} |
|---|---|---|---|---|
| 4.2 | Na/acetate | 0 | 15.3 | 48.7 |
| 4.2 | Na/acetate | 150 | −0.77 | 43 |
| 6.5 | His/acetate | 0 | 2.7 | 53.5 |
| 6.5 | His/acetate | 150 | −0.58 | 54.9 |

The addition of sodium chloride resulting in high ionic strength however has no clear effect on thermodynamic stability. According to results shown at Table 2, the addition of sodium chloride caused decrease in $A_2$ values. These values indicated that higher isotonic strength is not beneficial due to reduced existing repulsive interaction and no clear effect on conformational stability. Thus, the formulations in the present invention do not include salt component.

Example 3: Evaluation of Sorbitol Addition on Stability of Selected hFc-Fused G-CSF Formulations Sorbitol was evaluated as a stabilizer candidate amongst others, since many other candidates are not stable for long time in low pH. Sorbitol (5%) was added to formulation and then $T_{onset}$ and $A_2$ values were measured.

TABLE 3

Conformational and colloidal stability evaluation of 20 mg/mL hy-Fc fused G-CSF in 5% sorbitol containing formulations

| pH | Buffer [10 mM] | Stabilizer 5% | $A_2$ [mol*mL*g$^{-2}$] | $T_{onset}$ {° C.} |
|---|---|---|---|---|
| 4.2 | Na/acetate | – | 15.3 | 48.7 |
| 4.2 | Na/acetate | Sorbitol | 15.7 | 49.9 |
| 6.5 | His/acetate | – | 2.7 | 53.5 |
| 6.5 | His/acetate | Sorbitol | 1.87 | 53.5 |

According to results shown at Table 3, presence of sorbitol revealed slight conformational stabilizing effect at pH 4.2, but no effect at pH 6.5. Therefore, in this invention, a stabilizer is necessary to achieve desired colloidal and thermal stability. The preferred stabilizer in present invention is pharmaceutical grade Sorbitol in 5%.

Example 4: Evaluation of Surfactant Effect on Selected Formulations

For determination ideal surfactant, either 0.1% Poloxamer 188 (P188) or 0.02% Polysorbate 20 (PS20) or 0.02% Polysorbate 80 (PS80) was added to 10 mM sodium-acetate at pH 4.2 and histidine-acetate at pH 6.5 with 5% sorbitol formulations. These liquid hFc-Fused G-CSF formulations, listed in Table 4 were subjected to accelerated stability studies under 40° C. for 2 weeks to determine the potential stability of the protein over its shelf-life. These accelerated studies are usually performed at temperatures above the proposed storage conditions and the data are then used to estimate the activation energy for the degradation reactions assuming Arrhenius kinetics (Cleland et al., *Critical Reviews in Therapeutic Drug Carrier Systems* 10(4): 307-377 (1993)). The activation energy is then used to calculate the expected shelf-life of the protein formulation at the proposed storage conditions. Additionally, stability of formulations (Table 4) was evaluated under freeze-thaw stress. Stability was monitored against turbidity, monomeric and hydrophobic purity, and electrophoreticity in terms of molecular weight and isoelectric point.

TABLE 4

Formulation matrix to determine ideal surfactant for of 20 mg/mL hyFc fused G-CSF containing formulations.

| Formulations | pH | Buffer | Stabilizer | Surfactant | Packaging system |
|---|---|---|---|---|---|
| Formulation 1 (F1) | 4.2 | 10 mM Na/acetate | 5% sorbitol | — | Siliconized syringe |
| Formulation 2 (F2) | 4.2 | 10 mM Na/acetate | 5% sorbitol | +0.1% P188 | |
| Formulation 3 (F3) | 4.2 | 10 mM Na/acetate | 5% sorbitol | +0.02% PS20 | |
| Formulation 4 (F4) | 4.2 | 10 mM Na/acetate | 5% sorbitol | +0.02% PS80 | |
| Formulation 5 (F5) | 6.5 | 10 mM His/acetate | 5% sorbitol | — | Siliconized syringe |
| Formulation 6 (F6) | 6.5 | 10 mM His/acetate | 5% sorbitol | +0.1% P188 | |
| Formulation 7 (F7) | 6.5 | 10 mM His/acetate | 5% sorbitol | +0.02% PS20 | |
| Formulation 8 (F8) | 6.5 | 10 mM His/acetate | 5% sorbitol | +0.02% PS80 | |

Results revealed that all formulations are stable against freeze-thaw stress (Table 5-10). Also, it is an embodiment of this study that Poloxamer 188 (P188) containing formulations showed higher stability than Polysorbate 20 (PS20) and Polysorbate 80 (PS80) containing formulations and control formulations, under accelerated stability condition (40° C. for 2 weeks) (Table 5-10). Therefore, Poloxamer 188 or Pluronic F68 is included in the present invention as surfactant to minimize aggregation risk of hyFc-Fused G-CSF during storage and during transport conditions.

TABLE 5

Turbidity results of F1-F4 under 40° C. for 2 weeks and under freeze-thaw stress, n = 4.

| | Turbidity [NTU] | | | | | | | |
|---|---|---|---|---|---|---|---|---|
| | F1 | | F2 | | F3 | | F4 | |
| | Mean | SD | Mean | SD | Mean | SD | Mean | SD |
| t = 0 | 4.6 | 0.6 | 4.0 | 0.6 | 3.0 | 0.5 | 2.9 | 0.6 |
| Freeze/Thaw | 4.2 | 0.6 | 3.9 | 0.3 | 4.0 | 0.4 | 4.1 | 0.1 |
| Thermal stress (2 weeks 40° C.) | 6.2 | 1.3 | 5.5 | 0.8 | 6.5 | 0.4 | 6.4 | 0.7 |

TABLE 6

Turbidity results of F5-F8 under 40° C. for 2 weeks and under freeze-thaw stress, n = 4.

| | Turbidity [NTU] | | | | | | | |
|---|---|---|---|---|---|---|---|---|
| | F5 | | F6 | | F7 | | F8 | |
| | Mean | SD | Mean | SD | Mean | SD | Mean | SD |
| t = 0 | 7.3 | 0.4 | 6.9 | 1.0 | 7.6 | 0.7 | 7.0 | 0.8 |
| Freeze/Thaw | 7.4 | 0.9 | 7.5 | 1.1 | 7.8 | 0.2 | 6.7 | 0.5 |
| Thermal stress (2 weeks 40° C.) | 85.5 | 33.7 | 97.7 | 3.6 | 113.2 | 13.8 | 105.2 | 16.3 |

TABLE 7

Percent monomeric content of F1-F4 under 40° C. for 2 weeks and under freeze-thaw stress determined by SEC-HPLC, n = 4.

| | rel. Monomer content [%] | | | | | | | |
|---|---|---|---|---|---|---|---|---|
| | F1 | | F2 | | F3 | | F4 | |
| | Mean | SD | Mean | SD | Mean | SD | Mean | SD |
| t = 0 | 99.5 | 0.1 | 99.5 | 0.1 | 99.4 | 0.1 | 99.4 | 0.2 |
| Freeze/Thaw | 98.5 | 0.9 | 98.5 | 0.6 | 98.9 | 0.4 | 98.8 | 0.2 |
| Thermal stress (2 weeks 40° C.) | 85.7 | 0.9 | 86.3 | 1.4 | 58.9 | 0.5 | 66.5 | 0.5 |

TABLE 8

Percent monomeric content of F5-F8 under 40° C. for 2 weeks and under freeze-thaw stress determined by SEC-HPLC, n = 4.

| | rel. Monomer content [%] | | | | | | | |
|---|---|---|---|---|---|---|---|---|
| | F5 | | F6 | | F7 | | F8 | |
| | Mean | SD | Mean | SD | Mean | SD | Mean | SD |
| t = 0 | 98.5 | 0.7 | 98.1 | 0.7 | 98.6 | 0.4 | 98.3 | 0.1 |
| Freeze/Thaw | 98.2 | 0.7 | 98.1 | 0.7 | 98.4 | 0.3 | 98.1 | 0.1 |
| Thermal stress (2 weeks 40° C.) | 50.3 | 0.4 | 49.0 | 0.2 | 25.1 | 0.2 | 26.7 | 0.8 |

TABLE 9

Percent hydrophobic content of F1-F4 under 40° C. for 2 weeks and under freeze-thaw stress determined by RP-HPLC, n = 4.

| | rel. Main Peak content [%] | | | | | | | |
|---|---|---|---|---|---|---|---|---|
| | F1 | | F2 | | F3 | | F4 | |
| | Mean | SD | Mean | SD | Mean | SD | Mean | SD |
| t = 0 | 97.0 | 0.1 | 96.7 | 0.3 | 96.5 | 0.1 | 96.7 | 0.1 |
| Freeze/Thaw | 96.8 | 0.1 | 96.8 | 0.1 | 96.3 | 0.2 | 96.5 | 0.1 |
| Thermal stress (2 weeks 40° C.) | 86.5 | 0.1 | 87.4 | 0.1 | 69.3 | 0.1 | 76.6 | 0.2 |

TABLE 10

Percent hydrophobic content of F5-F8 under 40° C. for 2 weeks and under freeze-thaw stress determined by RP-HPLC, n = 4.

| | rel. Main Peak content [%] | | | | | | | |
|---|---|---|---|---|---|---|---|---|
| | F5 | | F6 | | F7 | | F8 | |
| | Mean | SD | Mean | SD | Mean | SD | Mean | SD |
| t = 0 | 96.6 | 0.1 | 96.5 | 0.1 | 96.4 | 0.1 | 96.5 | 0.1 |
| Freeze/Thaw | 96.5 | 0.1 | 96.4 | 0.0 | 96.4 | 0.0 | 96.4 | 0.1 |
| Thermal stress (2 weeks 40° C.) | 64.0 | 1.4 | 63.3 | 0.5 | 41.2 | 0.7 | 41.3 | 0.3 |

Figure 2:
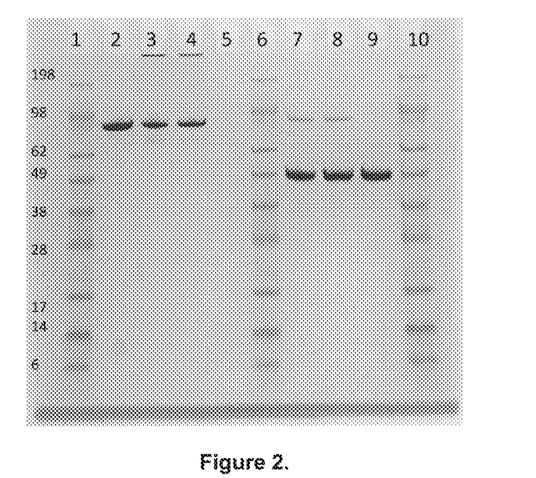
FIG. 2. Test for disulfide shuffling. Samples of variant #F5 and #F6 (stored for 2 weeks at 40° C.) were analyzed under reducing and non-reducing conditions. Line 1: Marker, Line 2: GX-G3 Ref non-reduced, Line 3: #F5 non-reduced, Line 4: #F6 non-reduced, Line 5: empty, Line 6: Marker, Line 7: #F5 reduced, Line 8: #F6 reduced, Line 9: Reference reduced, Line 10: Marker.
Figure 3:
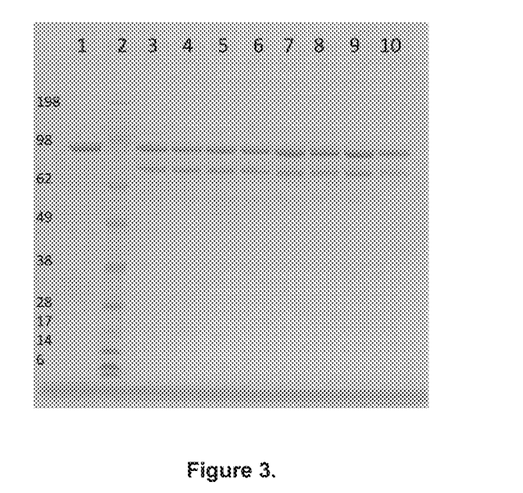
FIG. 3. SDS-PAGE thermal stress at 40° C. for 2 weeks: Line 1: Reference, Line 2: Marker, Line 3-6: #F3, Line 7-10: #F4.

In the same study, in pH 4.2 formulations and in its sub-variants, the main degradation products were fragments that are formed most likely due to hydrolysis. At pH 6.5 and its sub-variants covalently bound aggregates, due to di-sulfide shuffling, were found (FIGS. 2 & 3).

Example 5: Optimization and Long Term Evaluation of Selected Formulation

Formulation 2 (Table 4) was selected as the most stable formulation in screened formulation and coded as Formulation 2A. On the other hand, many studies demonstrated that small alteration in formulation pH could be critical for formulation stability. For the determination of pH alteration effect and long term stability of determined formulations, formulations listed in Table 11 (Formulation 2A) and Table 12 (Formulation 2B), were prepared altering pH 4.2 and 4.6, respectively. Herein, pH alteration was obtained by addition of pharmaceutically acceptable acid or a base. Herein, the preferred acid is acetic acid and the preferred base is sodium hydroxide.

TABLE 11

Composition of Formulation 2A, Buffered at pH 4.2

| Function | Component | Quantity per mL |
|---|---|---|
| Active ingredient | hy-Fc fused G-CSF | 20 mg |
| Stabilizer | Sorbitol | 50 mg |
| Surfactant | Poloxamer 188 (Pluronic F68) | 1 mg |
| Buffering agent | Sodium Acetate Trihydrate | 0.16 mg |
| Buffering agent | Acetic acid/ Sodium hydroxide | q.s.* |

*Quantum satis

TABLE 12

Composition of Formulation 2B, Buffered at pH 4.6

| Function | Component | Quantity per mL |
|---|---|---|
| Active ingredient | hy-Fc fused G-CSF | 20 mg |
| Stabilizer | Sorbitol | 50 mg |
| Surfactant | Poloxamer 188 (Pluronic F68) | 1 mg |
| Buffering agent | Sodium Acetate Trihydrate | 0.16 mg |
| Buffering agent | Acetic acid/ Sodium hydroxide | q.s.* |

*Quantum satis

Prior to the stability study, thermodynamic and colloidal stability of the prepared formulations were examined (Table 13).

TABLE 13

Colloidal and thermodynamic properties of Formulation 2A and 2B

| Formulation | $A_2$ [$10^{-4}$ mol*mL*$g^{-2}$] | $T_{onset}$ {° C.} |
|---|---|---|
| Formulation 2A | 21.1 | 53.6 |
| Formulation 2B | 5.1 | 51.2 |

Stability guidance of EMEA denotes that a minimum of six months stability data at the time of submission should be submitted in cases where storage periods greater than six months are requested. Therefore real time real condition stability test was performed at 2-8° C., accelerated stability test was performed at 25° C. for 6 months. Results are given at Table 14-17.

TABLE 14

Percent monomeric content of Formulation 2A and 2B determined by SEC-HPLC at 2-8° C., (n = 2).

| | rel. Monomer peak area by SEC-HPLC [%] | |
|---|---|---|
| 2-8° C. | Formulation 2A | Formulation 2B |
| t = 0 | 98.9 | 98.7 |
| 2 weeks | 98.9 | 98.8 |
| 1 month | 98.5 | 98.5 |
| 3 months | 98.5 | 98.6 |
| 6 months | 98.6 | 98.6 |

TABLE 15

Percent monomeric content of Formulation 2A and 2B determined by SEC-HPLC at 25° C., (n = 2).

| | rel. Monomer peak area by SEC-HPLC [%] | |
|---|---|---|
| 25° C. | Formulation 2A | Formulation 2B |
| t = 0 | 98.9 | 98.7 |
| 2 weeks | 98.8 | 98.9 |
| 1 month | 98.7 | 98.7 |

TABLE 15-continued

Percent monomeric content of Formulation 2A and 2B determined by SEC-HPLC at 25° C., (n = 2).

| 25° C. | rel. Monomer peak area by SEC-HPLC [%] | |
| --- | --- | --- |
|  | Formulation 2A | Formulation 2B |
| 3 months | 99.0 | 97.8 |
| 6 months | 83.8 | 81.8 |

TABLE 16

Percent hydrophobic content of Formulation 2A and 2B determined by RP-HPLC at 2-8° C., (n = 2).

| 2-8° C. | rel. Main peak area by RP-HPLC [%] | |
| --- | --- | --- |
|  | Formulation 2A | Formulation 2B |
| t = 0 | 97.2 | 97.5 |
| 2 weeks | 97.1 | 97.1 |
| 1 month | 97.0 | 97.0 |
| 3 months | 96.7 | 96.6 |
| 6 months | 96.1 | 96.3 |

TABLE 17

Percent hydrophobic content of Formulation 2A and 2B determined by RP-HPLC at 25° C. (n = 2).

| 25° C. | rel. Main peak area by RP-HPLC [%] | |
| --- | --- | --- |
|  | Formulation 2A | Formulation 2B |
| t = 0 | 97.2 | 97.5 |
| 2 weeks | 96.0 | 96.0 |
| 1 month | 95.0 | 94.7 |
| 3 months | 90.8 | 89.6 |
| 6 months | 86.3 | 84.6 |

It was shown that Formulation 2A and 2B were found stable at least 6 months under real time and real temperature conditions (Table 14-17). Thus, in this present invention, both pH 4.2 and 4.6 formulations were revealed to provide long-term stability to hy-Fc fused G-CSF under real-time-real stability and accelerated conditions.

Example 6: Evaluation of Organic Solvent Effect on Stability of Hy-Fc Fused G-CSF Formulation The present formulation leads to develop an improved formulation to overcome degradation by the cleavage of G-CSF molecule thereof further decomposition by using an organic solvent, propylene glycol (PG).

During formulation development, the influence of pH and the presence of propylene glycol on hy-Fc fused G-CSF stability were evaluated (Table 18).

TABLE 18

Study matrix evaluating the influence of pH and the presence of propylene glycol on 20 mg/mL of Hy-Fc fused G-CSF stability.

| Formulation Code | pH | Formulation Code + Percent of propylene glycol (PG) | Packaging system |
| --- | --- | --- | --- |
| F2A | 4.2 | Only Formulation 2A | Siliconized syringe |
| F2A + 10PG | 4.2 | Formulation 2A + 10% PG | |
| F2A + 20PG | 4.2 | Formulation 2A + 20% PG | |

TABLE 18-continued

Study matrix evaluating the influence of pH and the presence of propylene glycol on 20 mg/mL of Hy-Fc fused G-CSF stability.

| Formulation Code | pH | Formulation Code + Percent of propylene glycol (PG) | Packaging system |
| --- | --- | --- | --- |
| F2B | 4.6 | Only Formulation 2B | |
| F2B + 10PG | 4.6 | Formulation 2B + 10% PG | |
| F2B + 20PG | 4.6 | Formulation 2B + 20% PG | |

The stability of the hy-Fc fused G-CSF was studied at a pH of 4.2 and 4.6 of 10 mM sodium-acetate buffer comprised of 0.01% Pluronic F-68, 5% Sorbitol and either with or without 10% PG or 20% PG. Samples comprising of 20 mg/mL active ingredient, were placed at 25° C. and 2-8° C. for 6 months. Prior to the stability study, the syringeability as well as the thermodynamic and colloidal stability of the formulations were examined (Table 19).

TABLE 19

Colloidal and thermodynamic properties of Formulation 2A and 2B after organic solvent exchange.

| Formulation | $A_2$ [$10^{-4}$ mol*mL*$g^{-2}$] | $T_{onset}$ {° C.} |
| --- | --- | --- |
| F2A | 21.1 | 53.6 |
| F2A + 10PG | 22.7 | 50.5 |
| F2A + 20PG | 19.9 | 45.2 |
| F2B | 5.1 | 51.2 |
| F2B + 10PG | 5.0 | 47.6 |
| F2B + 20PG | 4.7 | 45.0 |

As one embodiment of this study is that the push-out forces for all formulations was below 10 N and thus well acceptable for a drug administered by an injection. Formulations containing propylene glycol showed a slightly higher push-out force compared to formulations without propylene glycol. The pH had no influence on the results.

According to results at Table 19, the colloidal stability of hy-Fc fused G-CSF is higher at lower pH. The presence of 10% propylene glycol slightly increases the repulsive protein interactions, thus the colloidal stability, whereas 20% propylene glycol does not. The thermodynamic stability of hy-Fc fused G-CSF is also slightly higher at low pH.

As another embodiment, the same study revealed that the main degradation pathway of hy-Fc fused G-CSF is a chemical degradation and fragmentation, as the data showed that decrease in the monomer level was due to the increase of elevated low molecular weight impurities (Table 21). Aggregation due to disulfide shuffling of hy-Fc fused G-CSF was not observed in the same study.

As final embodiment of the same study, it was shown that the addition of propylene glycol has a beneficial effect on chemical stability, as set forth by the accelerated stability data (Table 20-23). However, 20% PG reduces the thermodynamic stability (Table 19) and thus addition of 10% PG is preferred thereof.

TABLE 20

Percent monomeric content of 20 mg/mL hy-Fc fused CSF determined by SEC-HPLC at 2-8° C., (n = 2).

| 2-8° C. | F2A | F2A + 10PG | F2A + 20PG | F2B | F2B + 10PG | F2B + 20PG |
|---|---|---|---|---|---|---|
| rel. Monomer peak area by SEC-HPLC [%] | | | | | | |
| t = 0 | 98.9 | 98.7 | 98.8 | 98.7 | 98.6 | 98.3 |
| 2 weeks | 98.9 | 98.8 | 98.9 | 98.8 | 98.7 | 98.5 |
| 1 month | 98.5 | 97.0 | 98.7 | 98.5 | 98.5 | 98.2 |
| 3 months | 98.5 | 98.5 | 98.7 | 98.6 | 98.3 | 98.3 |
| 6 months | 98.6 | 98.5 | 98.8 | 98.6 | 98.3 | 98.2 |

TABLE 21

Percent monomeric content of 20 mg/mL hy-Fc fused CSF determined by SEC-HPLC at 25° C., (n = 2).

| 25° C. | F2A | F2A + 10PG | F2A + 20PG | F2B | F2B + 10PG | F2B + 20PG |
|---|---|---|---|---|---|---|
| rel. Monomer peak area by SEC-HPLC [%] | | | | | | |
| t = 0 | 98.9 | 98.7 | 98.8 | 98.7 | 98.6 | 98.3 |
| 2 weeks | 98.8 | 98.9 | 99.4 | 98.9 | 98.8 | 99.0 |
| 1 month | 98.7 | 98.9 | 99.2 | 98.7 | 98.6 | 98.4 |
| 3 months | 99.0 | 99.2 | 98.9 | 97.8 | 99.1 | 98.0 |
| 6 months | 83.8 | 84.7 | 85.6 | 81.8 | 82.8 | 83.3 |

TABLE 22

Percent hydrophobic content of 20 mg/mL hy-Fc fused CSF determined by RP-HPLC at 2-8° C., (n = 2).

| 2-8° C. | F2A | F2A + 10PG | F2A + 20PG | F2B | F2B + 10PG | F2B + 20PG |
|---|---|---|---|---|---|---|
| rel. Main peak area by RP-HPLC [%] | | | | | | |
| t = 0 | 97.2 | 97.1 | 97.4 | 97.5 | 97.5 | 97.5 |
| 2 weeks | 97.1 | 97.2 | 97.2 | 97.1 | 97.2 | 97.2 |
| 1 month | 97.0 | 96.8 | 97.1 | 97.0 | 97.2 | 97.1 |
| 3 months | 96.7 | 96.8 | 96.9 | 96.6 | 96.9 | 96.9 |
| 6 months | 96.1 | 96.4 | 96.4 | 96.3 | 96.5 | 96.4 |

TABLE 23

Percent hydrophobic content of 20 mg/mL hy-Fc fused CSF determined by RP-HPLC at 25° C., (n = 2).

| 25° C. | F2A | F2A + 10PG | F2A + 20PG | F2B | F2B + 10PG | F2B + 20PG |
|---|---|---|---|---|---|---|
| rel. Main peak area by RP-HPLC [%] | | | | | | |
| t = 0 | 97.2 | 97.1 | 97.4 | 97.5 | 97.5 | 97.5 |
| 2 weeks | 96.0 | 96.1 | 96.3 | 96.0 | 95.9 | 96.3 |
| 1 month | 95.0 | 95.1 | 95.6 | 94.7 | 95.0 | 95.2 |
| 3 months | 90.8 | 91.0 | 91.4 | 89.6 | 90.3 | 90.9 |
| 6 months | 86.3 | 87.1 | 88.0 | 84.6 | 86.0 | 87.3 |

Stability of formulations, listed in Table 18, was found to last at least 6 months under real-time, real-temperature and accelerated conditions. And PG addition had a beneficial effect in the chemical stability of formulations. Thus, presence of PG could be an opportunity to overcome degradation by the cleavage of G-CSF as one could interpret from hydrophobic purity change at 25° C., monitored by RP-HPLC (Table 23). Thus, in this present invention, addition of %20 or less PG as organic was revealed to further enhance the long-term stability of hy-Fc fused G-CSF under real-time, real-temperature and accelerated conditions.

Example 7: Further Evaluation of pH Effect on Real-Time Stability of Hy-Fc Fused G-CSF Formulation In order to fully investigate the effect of pH on real-time stability of hy-Fc fused G-CSF, pH 4.0 and pH 4.4 with and without 10% propylene glycol PG formulations (Table 19) were studied at 2-8° C. for 6 months.

Hy-Fc fused G-CSF of 20 mg/mL active ingredient was studied at a pH of 4.0 and 4.4 of 10 mM sodium-acetate buffer comprised of 0.01% Pluronic F-68, 5% Sorbitol contains both with and without 10% PG.

TABLE 24

Composition of Formulation 2C, Buffered at pH 4.0

| Function | Component | Quantity per mL |
|---|---|---|
| Active ingredient | hy-Fc fused G-CSF | 20 mg |
| Stabilizer | Sorbitol | 50 mg |
| Surfactant | Poloxamer 188 (Pluronic F68) | 1 mg |
| Buffering agent | Sodium Acetate Trihydrate | 0.16 mg |
| Buffering agent | Acetic acid/ Sodium hydroxide | q.s.* |

*Quantum satis

TABLE 25

Composition of Formulation 2D, Buffered at pH 4.4

| Function | Component | Quantity per mL |
|---|---|---|
| Active ingredient | hy-Fc fused G-CSF | 20 mg |
| Stabilizer | Sorbitol | 50 mg |
| Surfactant | Poloxamer 188 (Pluronic F68) | 1 mg |
| Buffering agent | Sodium Acetate Trihydrate | 0.16 mg |
| Buffering agent | Acetic acid/ Sodium hydroxide | q.s.* |

*Quantum satis

TABLE 26

Study matrix evaluating the influence of pH and the presence of propylene glycol on 20 mg/mL of Hy-Fc fused G-CSF stability.

| Formulation Code | pH | Formulation Code + Percent of propylene glycol (PG) | Packaging system |
|---|---|---|---|
| F2C | 4.0 | Only Formulation 2C | Siliconized syringe |
| F2C + 10PG | 4.0 | Formulation 2C + 10% PG | |
| F2D | 4.4 | Only Formulation 2D | |
| F2D + 10PG | 4.4 | Formulation 2D + 10% PG | |

TABLE 27

Percent monomeric content of 20 mg/mL hy-Fc fused CSF determined by SEC-HPLC at 2-8° C., (n = 2).

| 2-8° C. | F2C | F2C + 10PG | F2D | F2D + 10PG |
|---|---|---|---|---|
| rel. Main peak area by SEC-HPLC [%] | | | | |
| t = 0 | 99.7 | 99.7 | 99.7 | 99.7 |
| 1 month | 99.5 | 99.5 | 99.5 | 99.5 |

TABLE 27-continued

Percent monomeric content of 20 mg/mL hy-Fc fused CSF determined by SEC-HPLC at 2-8° C., (n = 2).

| | rel. Main peak area by SEC-HPLC [%] | | | |
|---|---|---|---|---|
| 2-8° C. | F2C | F2C + 10PG | F2D | F2D + 10PG |
| 3 months | 99.7 | 99.6 | 99.7 | 99.6 |
| 6 months | 99.6 | 99.6 | 99.6 | 99.6 |

TABLE 28

Percent hydrophobic content of 20 mg/mL hy-Fc fused CSF determined by RP-HPLC at 2-8° C., (n = 2).

| | rel. Main peak area by RP-HPLC [%] | | | |
|---|---|---|---|---|
| 2-8° C. | F2C | F2C + 10PG | F2D | F2D + 10PG |
| t = 0 | 97.3 | 96.7 | 97.5 | 96.8 |
| 1 month | 96.3 | 96.4 | 96.5 | 96.5 |
| 3 months | 95.9 | 95.9 | 95.9 | 96.0 |
| 6 months | 95.6 | 96.3 | 95.7 | 95.8 |

Figure 4:
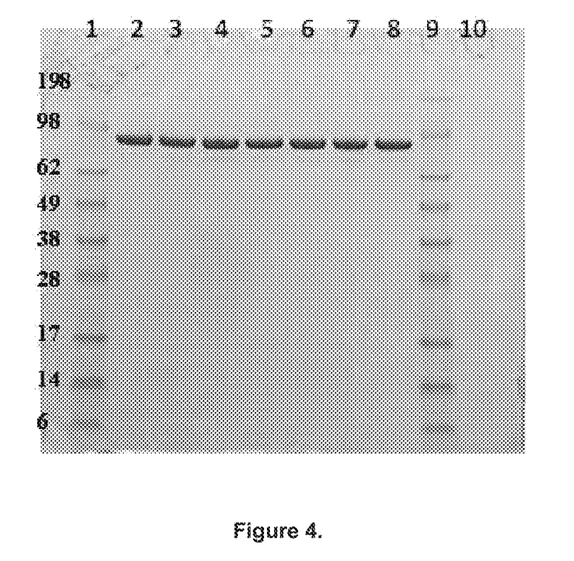
FIG. 4. SDS-PAGE analysis at 2-8° C. at t=6 months: Line 1, 9: Marker, Line 2, 5, 6: Reference, Line 3: #F2C, Line 4: #F2C+10% PG, Line 7: #F2D, Line 8: #F2D+10% PG, Line 10: Empty.
Figure 5:
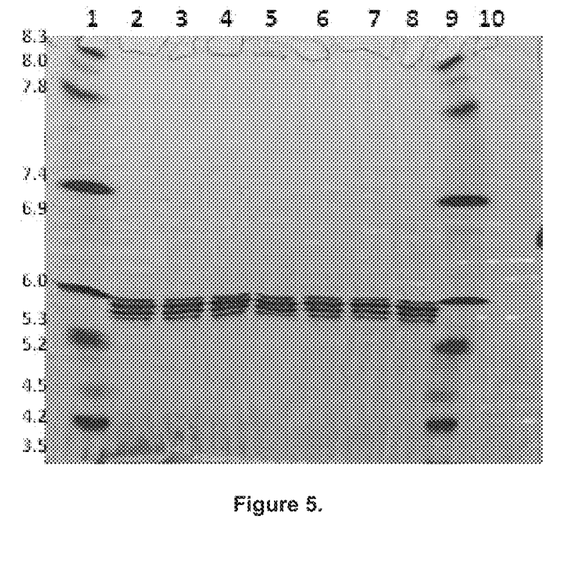
FIG. 5. Gel-IEF analysis at 2-8° C. at t=6 months: Line 1, 9: Marker, Line 2, 5, 6: Reference, Line 3: #F2C, Line 4: #F2C+10% PG, Line 7: #F2D, Line 8: #F2D+10% PG, Line 10: Empty.

As an embodiment of this study, it was revealed that hy-Fc fused G-CSF is stable at the chosen conditions, justified with SEC-HPLC, RP-HPLC, SDS-PAGE and Gel-IEF analyses (Table 27-28, FIG. 4-5). Neither aggregates nor cleaved forms of hy-Fc fused G-CSF were observed in the study. Thus, in this present invention, both pH 4.0 and 4.4 formulations were revealed to provide long-term stability to hy-Fc fused G-CSF under real-time, real temperature and accelerated conditions.

TABLE 29

Composition of the hy-Fc fused G-CSF 20 mg/mL solution.

| Function | Component | Reference to Standards | Quantity per mL |
|---|---|---|---|
| Stabilizer | Sorbitol | NF | 50 mg |
| Surfactant | Poloxamer 188 (Pluronic F68) | NF | 1 mg |
| Buffering agent | Sodium Acetate Trihydrate | USP | 0.16 mg |
| Buffering agent | Acetic acid/ Sodium hydroxide | USP | q.s.* |
| Organic solvent | Propylene Glycol | USP | 0.1 mL |

*Quantum satis

To conclude, as utilized herein, hybrid Fc fusion G-CSF formulation, as described in Table 29, is shown to be stable at a pH range between 3.8-6.5, preferably 4.0-4.6. Herein, in the present invention, the formulation is comprised of buffer system, surfactant, stabilizer and/or PG as organic solvent.

In the present invention, the buffer system may comprise Sodium Acetate Trihydrate salt and Acetic acid/Sodium hydroxide.

The present invention may comprise sorbitol as a surfactant preferably at a concentration of from 0.08 w/v % to 0.15 w/v %, and sorbitol as a stabilizer preferably at a concentration of from 3.0 w/v % and 7.0 w/v % based on the total volume of the liquid formulation, wherein weight ratio of sorbitol to protein is between 3:2 to 7:2, preferably 5:2.

The present invention may comprise of 20 v/v % or less PG (Sigma, Switzerland), preferably 10 v/v % or less PG based on the total volume of the liquid formulation in order to reduce aqueous content that assists to facilitate cleavage process of G-CSF by means of hydrolysis at acidic pH.

---

The invention claimed is:

1. A stable formulation of hybrid fragment crystallizable (Fc) fusion Granulocyte colony stimulating factor (G-CSF) protein, comprising a therapeutically effective amount of the hybrid Fc fusion G-CSF protein in a concentration from 10 mg/mL to 80 mg/mL,
   wherein a pH value of the formulation is between 4.2 and 4.6 with having sodium acetate trihydrate and acetic acid/sodium hydroxide buffer system and the formulation comprises sorbitol as a stabilizer and a non-ionic surfactant selected from the group consisting of poloxamer 188, polysorbate 20, and polysorbate 80, and a combination thereof, and
   wherein the hybrid Fc fusion G-CSF protein comprises consecutive amino acid residues at position 31 through position 449 of SEQ ID NO: 1.

2. The stable formulation according to claim 1, wherein the sorbitol is in a concentration from 3.0 w/v % and 7.0 w/v % based on total volume of the formulation.

3. The stable formulation according to claim 1, wherein a weight ratio of the sorbitol to the hybrid Fc fusion G-CSF is between 3:2 to 7:2.

4. The stable formulation according to claim 3, wherein the weight ratio of the sorbitol to the hybrid Fc fusion G-CSF is 5:2.

5. The stable formulation according to claim 1, wherein the surfactant is poloxamer 188.

6. The stable formulation according to claim 5, wherein the poloxamer 188 is in a concentration from 0.08 w/v % to 0.15 w/v % based on total volume of the formulation in liquid form.

7. The stable formulation according to claim 1, wherein the hybrid Fc fusion G-CSF is in a concentration from 20 mg/mL to 40 mg/mL.

8. The stable formulation according to claim 1, which further comprises propylene glycol as an organic solvent.

9. The stable formulation according to claim 8, wherein the propylene glycol is at a concentration of 20 v/v % or less based on a total volume of the formulation in liquid form.

10. The stable formulation according to claim 9, wherein the propylene glycol is at a concentration of 10 v/v % or less based on the total volume of the formulation in liquid form.

* * * * *